United States Patent [19]

Behrenz et al.

[11] 4,123,518

[45] Oct. 31, 1978

[54] INSECTICIDAL PHOSPHATE ESTER-BASED SOLID COMPOSITION WITH DEPOT GAS ACTION

[75] Inventors: Wolfgang Behrenz, Overath-Steinenbrueck; Klaus Burkhardt, Krefeld, both of Germany

[73] Assignee: Bayer Aktiengesellschaft, Leverkusen, Germany

[21] Appl. No.: 772,390

[22] Filed: Feb. 28, 1977

Related U.S. Application Data

[63] Continuation of Ser. No. 624,215, Oct. 20, 1975, abandoned.

[30] Foreign Application Priority Data

Oct. 25, 1974 [DE] Fed. Rep. of Germany ....... 2450677

[51] Int. Cl.$^2$ ............................................. A01N 17/00
[52] U.S. Cl. ........................................ 424/78; 424/32; 424/219
[58] Field of Search ............................ 424/78, 219, 32

[56] References Cited

U.S. PATENT DOCUMENTS

| 3,608,062 | 9/1971 | Alfes et al. | 424/219 |
| 3,740,428 | 6/1973 | Soloway et al. | 424/219 |

Primary Examiner—V. D. Turner
Attorney, Agent, or Firm—Burgess, Dinklage & Sprung

[57] ABSTRACT

In a pesticidal preparation having a depot gas action, and comprising a phosphate ester in admixture with a solid carrier, the improvement wherein said phosphate ester comprises dimethyl-2,2-dichlorovinyl thiophosphate.

5 Claims, No Drawings

INSECTICIDAL PHOSPHATE ESTER-BASED SOLID COMPOSITION WITH DEPOT GAS ACTION

This is a continuation of application Ser. No. 624,215, filed Oct. 20, 1975, now abandoned.

The present invention relates to new preparations, having a depot gas action, comprising dimethyl-2,2-dichlorovinyl thiophosphate as a gassing agent, which acts automatically via the gas phase, and on solid carriers.

The use of dimethyl-2,2-dichlorovinyl phosphate (DDVP) in formulations which automatically act as gassing agents, in combating pests, has been known for a long time. Very diverse materials have been proposed as carriers for the above-mentioned active compound: macromolecular thermoplastic, thermosetting and elastomeric plastics or natural materials, such as wood, cardboard, asbestos, lime, gypsum, beeswax and montan wax. Further examples of suitable carriers are natural and synthetic rubber polyolefins such as polyethylene, polypropylene and copolymers of ethylene and propylene, polyacrylates and copolyacrylates of methyl acrylate, ethyl acrylate and methyl methacrylate, polyvinyl compounds such as polystyrene, polyvinyltoluene and polyvinyl acetate, polyvinyl halides and polyvinylidene halides such as polyvinyl chloride, polyvinyl fluoride and polyvinylidene chloride, polyvinyl acetals such as polyvinyl butyral, linear and branched polyesters and polyethers, and cellulose plastics such as cellulose acetate, cellulose propionate, cellulose butyrate and cellulose nitrate. Examples of further suitable carriers are unsaturated polyesters, epoxides, polyurethanes, phenol-formaldehyde, urea-formaldehyde and melamine-formaldehyde resins.

The polymers and copolymers of vinyl chloride (see DT-AS (German Published Pat. No.) 1,230,259) as well as unsaturated polyester systems (see DT-AS (German Published Pat. No.) 1,694,240 and DT-OS (German Published Pat. No.) 2,231,099) have been described as particularly preferred carriers, as have also polymeric acrylates and polymeric vinyl compounds such as polystyrene.

In addition to the active compound, the formulations frequently also contain auxiliaries such as plasticizers, stabilizers, vaporization regulators and fillers, depending on the nature of the carrier. Examples of possible plasticizers are dioctyl phthalate, alkanesulfonic acid aryl esters, trioctyl phosphate, triphenyl phosphate, dibutyl adipate, chlorinated paraffin, diisononyl phthalate, di-2-ethylhexyl adipate, di-2-ethylhexyl phthalate and di-2-ethylhexyl sebacate. Examples of suitable stabilizers are phenols, amines or lower nitrogen-containing heterocyclic compounds, as well as azo and hydrazo compounds, acid anhydrides, epoxides and elementary sulfur (DT-OS (German Published Pat. No.) 2,145,318), and also compounds which are usually employed for stabilizing macromolecular substances, such as, for example, organic cadmium compounds and lead compounds as heat stabilizers for polyvinyl chloride.

Examples of suitable vaporization regulators are palmitic acid ethyl ester, myristic acid isopropyl ester, di-n-butyl phthalate, 2-chloronaphthalene, camphor, benzoic acid, biphenyl, isobutyl benzoate and others, such as are described, for example, in East German Pat. No. 91,898 and also in DT-OS's (German Published Pat. Nos.) 1,954,501, 2,026,119 and 2,028,226.

Fillers may be, for example, fibers of glass, sisal, hemp, nettle, coir and flax, as well as titanium dioxide, iron oxides, kaolin, quartz and other inert materials.

The formulations in question are in most cases employed as moldings such as slabs, sheets, tapes, bars, spheres, foams, strips, films, tablets or granules. If, in the course of use, such a molding is, for example, brought into the living room or bedroom of a house, or placed, in the form of a neckband, round the neck of a domestic animal, the DDVP contained in the preparation is gradually released into the surrounding air, as a result of the vapor pressure of the DDVP or with the aid of heat sources, for example electrical energy, and thus automatically kills, via the gas phase, the pests present in the room and on domestic animals (see DT-AS (German Published Pat. No.) 1,230,259; British Patent specification No. 1,015,933; South African Pat. No. 62/371; DT-AS (German Published Pat. No.) 1,694,240; DT-OS's (German Published Pat. No.) 1,941,046 and 2,231,099; and DT-AS (German Published Pat. No.) 1,802,684).

The moldings can either be employed for use directly or be surrounded by casings (quivers), which can be opened or closed completely or partially in order thereby periodically to interrupt the release of the DDVP or to regulate the amount of active compound released.

A problem of using DDVP in these automatic gassing moldings is that the release of the active compound must be so controlled that sufficient active compound is released into the air of the room to kill the pests reliably while the humans and domestic animals present in the room are not harmed.

It is accordingly an object of the present invention to provide a composition having a depot gas action which is characterized by marked insecticidal activity with markedly lower mammalian toxicity than DDVP.

It has now been found that this object can be realized if in depot gas active compositions containing solid carriers and DDVP, the DDVP is replaced by dimethyl-2,2-dichlorovinyl thiophosphate, i.e., thio-DDVP.

It is surprising that thio-DDVP would be suitable for this purpose since no compound other than DDVP has gained commercial importance for such use, notwithstanding that South African Pat. No. 62/371 describes combinations with a large number of other phosphoric acid esters and the corresponding thiophosphates. Moreover, with regard to the thiophosphates, DT-AS (German Published Pat. No.) 1,230,259 discloses that they are less compatible with macromolecular substances than are the phosphoric acid esters in question. Furthermore, it is generally known that thiophosphoric acid esters have a lower insecticidal power than the corresponding phosphates and this extends also to thio-DDVP in comparison with DDVP, as shown in comparison Example 1 hereinbelow. It is accordingly surprising that thio-DDVP could be formulated into solid preparations, and that they then would be sufficiently active insecticidally by way of depot gas action while being of lower mammalian toxicity.

As such preparations, it is possible to use combinations which consist of thio-DDVP and macro-molecular thermoplastic, elastomeric or thermosetting plastics or natural materials such as wood, cardboard, asbestos, lime, gypsum, felt, beeswax or montan wax as carriers.

In addition to the active compound, the preparations in question can, depending on the nature of the carrier, also contain the above-mentioned auxiliaries such as, for example, plasticizers, stabilizers, vaporization regulators, vaporization inhibitors or vaporization promoters, and fillers. The preparations may be used in the form of shaped articles such as slabs, sheets, tapes, bars, spheres, foams, strips, films, tablets, neckbands or granules. They can be surrounded by casings which permit a controllable full or reduced release of active compound.

The preparations according to the invention, based on thio-DDVP as an automatically acting gassing agent, and solid carriers, can be used to combat a great diversity of species of pests. The thio-DDVP to be used as the active compound according to the invention is known from the literature and can be prepared, for example, in accordance with the process described in DT-OS (German Published Pat. No. ) 2,238,921.

Thus, for example, the carrier may be a naturally occurring material or derived from a naturally occurring material such as asbestos, lime or gypsum. Alternatively, it may comprise wood, cardboard or felt. It can comprise natural or synthetic macromolecular substances such as cellulose or keratin, or thermoplastic, thermosetting or elastomeric materials or mixtures of any of the foregoing. It may contain one or more auxiliaries or fillers such as plasticizers, stabilizers, vaporization promoters, vaporization inhibitors, glass fibers, textile fibers, pigments, dyestuffs, scents and quartz and the preparation may be contained in a casing which adjustably provides for full or reduced release of the gassing agent.

The proportions of the thio-DDVP and the other ingredients in the compositions can be generally the same as has heretofore been employed and disclosed in connection with DDVP, particularly in the patent publications referred to hereinabove, the disclosures of which are incorporated herein by reference.

The following examples explain the invention in more detail, with "parts" denoting parts by weight. The poorer insecticidal action of dimethyl-2,2-dichlorovinyl thiophosphate compared to DDVP is shown by the following comparison experiment:

EXAMPLE 1

Aerosol test

Test animals: Musca domestica
Solvent: Acetone

To produce a suitable preparation of active compound, the active compound was mixed, at a range of concentrations, with the stated solvent.

A wire cage which contained about 25 test animals was suspended in the centre of a gas-tight glass chamber of size 1 $m^3$. After the chamber had been closed again, 2 ml of the preparation of active compound were atomised in the chamber. The condition of the test animals was constantly checked from outside, through the glass walls, and the time required for a knock-down effect on 50% of the animals was determined.

The active compounds, amounts used and time after which 50% of the animals were lying on their backs ($LT_{50}$) can be seen from the table which follows:

Table 1

| Active compound | Aerosol test Amount used mg/$m^3$ | $LT_{50}$ |
|---|---|---|
| DDVP | 1 | 10'37" |
| Thio-DDVP | 1 | 19'15" |
| | 2 | 13'37" |
| | 3 | 11'40" |

Table 1-continued

| Active compound | Aerosol test Amount used mg/$m^3$ | $LT_{50}$ |
|---|---|---|
| | 4 | 9'20" |

It is therefore not surprising that the above-mentioned publications do not contain an example of the use of thio-DDVP, or that this active compound is not mentioned anywhere, even cursorily, as an example in a list.

EXAMPLE 2

A factor which proves particularly advantageous in the use, according to the invention, of thio-DDVP is that compared to DDVP the active compound, and its degradation products, decomposition products and possible by-products have a lower toxicity to warm-blooded animals, as can be seen from the table which follows:

Table 2

| | | $LD_{50}$ male rats |
|---|---|---|
| Acute oral toxicity | DDVP | 62 mg/kg |
| | Thio-DDVP | 773 mg/kg |
| | | $LC_{50}$ male rats |
| Acute inhalation toxicity (4 hours' exposure) | DDVP | 340 mg/$m^3$ |
| | Thio-DDVP | >477 mg/$m^3$* |

*This concentration, which is the maximum possible in the experiment, was tolerated without symptoms by the animals.

In each of Examples 3 and 4 the carrier used was a mixture of 440 parts of an unsaturated polyester (prepared by polycondensation of 205.8 parts of maleic anhydride, 725.2 parts of phthalic anhydride, 546.4 parts of 1,2-propanediol and 0.265 part of hydroquinone, and having an acid number of 42) and 240 parts of styrene (polyester mixture 1).

EXAMPLE 3

A homogeneous premix was prepared from 680 parts of polyester mixture 1,390 parts of thio-DDVP, 230 parts of $C_{10}$-$C_{18}$ alkanesulfonic acid phenyl ester and 27 parts of maleic anhydride. After adding 41 parts of benzoyl peroxide in dibutyl phthalate (50% strength) and 4 parts of a 10% strength solution of dimethylaniline in toluene, a cast sheet having a glass fiber content of 26% was produced by heating the mixture for about 30 minutes to 80°–100° C. in a closed mold in which a glass fiber mat (600 g/$m^2$) had been laid. The sheet was subsequently cut into shaped pieces of size 8 × 25 cm. The active compound content was 20 g.

EXAMPLE 3a (Comparison example)

Shaped pieces of size 8 × 25 cm and having an active compound content of 20 g were produced in the same manner as described in Example 1, but using DDVP as the active compound.

EXAMPLE 4

A homogeneous premix was prepared from 630 parts of polyester mixture 1 and 450 parts of thio-DDVP. After adding 36 parts of benzoyl peroxide in dibutyl phthalate (50% strength), a cast sheet having an asbestos content of 3.5 percent by weight was produced by heating for about 30 minutes to 80°-100° C. in a closed mold into which granular asbestos particles had been introduced. The sheet was subsequently cut into shaped pieces of size 8 × 25 cm, having an active compound content of 38%.

For examples 5 and 6, the carrier used was in each case a mixture of 730 parts of an unsaturated polyester (prepared by polycondensation of 262.8 parts of maleic anhydride, 926.8 parts of phthalic anhydride, 612 parts of 1,2-propanediol, 359.6 parts of dipropylene glycol and 0.214 part of hydroquinone, and having an acid number of 3.9) and 350 parts of styrene (polyester mixture 2).

EXAMPLE 5

A homogeneous premix was prepared from 665 parts of polyester mixture 2 and 475 parts of thio-DDVP. After adding 38 parts of benzoyl peroxide in dibutyl phthalate (50% strength), a cast sheet with a fabric content of 26 percent by weight was produced by heating for about 30 minutes to 80°-100° C. in a closed mold into which a fabric of polyacrylonitrile fibers (280 g/m$^2$) had been laid. The sheet was subsequently cut into shaped pieces of size 8 × 25 cm, having an active compound content of 24 g each.

EXAMPLE 5a (Comparison example)

A homogeneous premix, and shaped pieces of the same sizes and of the same active compound content, were prepared in the same manner as in Example 5, but using DDVP as the active compound.

EXAMPLE 6

A homogeneous premix was prepared from 438 parts of polyester mixture 2 and 299 parts of the thio-DDVP. After adding 26 parts of benzoyl peroxide in dibutyl phthalate (50% strength), a cast sheet with a fabric content of 26 percent by weight was produced by heating for about 30 minutes to 80°-100° C. in a closed mold into which a jute fabric (1,150 g/m$^2$) had been laid. The sheet was subsequently cut into shaped pieces of size 8 × 25 cm, having an active compound content of 25 g each.

EXAMPLE 6a (Comparison example)

A homogeneous premix, and shaped pieces of the same sizes and of the same active compound content, were prepared in the same manner as in Example 6, but using DDVP as the active compound.

EXAMPLE 7

Shaped pieces of size 8 × 25 cm were cut from 3 mm thick cardboard and impregnated with thio-DDVP. The active compound content in the cardboard was 30 g.

The pesticidal activity of the present formulations is illustrated in the following examples.

EXAMPLE 8

One shaped piece produced according to Example 3 and one shaped piece produced according to Example 3a were each pushed into a casing of fine wire mesh and suspended from the ceiling in the center of identical rooms of 50 m$^3$ cubic capacity. Four weeks later, 200 flies of the species Musca domestics were released in the rooms. In the room in which the shaped piece according to Example 3 was suspended, the flies dropped after 2 hours. In the room in which the shaped piece according to Example 3a was suspended, it required 3 hours for 100% of the flies to lie on their backs.

EXAMPLE 9

One shaped piece produced according to Example 5 and one shaped piece produced according to Example 5a were each pushed into a net-like quiver and suspended from the ceiling in the center of identical rooms of 40 m$^3$ cubic capacity. Immediately thereafter (0), and after 4, 8 and 12 weeks, 200 flies of the species Musca domestica were in each case exposed in the rooms. The flies did not come into direct contact with the shaped pieces. In each case, the percentage of animals which had fallen on their backs was determined 1 hour after exposing the flies. The results obtained can be seen from the table which follows:

Table 3

| Age of the shaped pieces, in weeks | percentage of animals lying on their backs after one hour | |
|---|---|---|
| | DDVP | Thio-DDVP |
| 0 | 80 | 100 |
| 4 | 70 | 95 |
| 8 | 60 | 90 |
| 12 | 20 | 50 |

EXAMPLE 10

One shaped piece produced according to Example 6 and one shaped piece produced according to Example 6a were each pushed into an open-pore quiver and suspended open in a room. After 2 weeks, the shaped piece according to Example 6 was first brought into a room of 43 m$^3$ cubic capacity and 300 flies of the species Musca domestica were released. The time after which 100% of the flies had fallen on their backs was determined. Thereafter the room was thoroughly sired and the same experiment was carried out with the shaped piece according to Example 6a. The results obtained are shown in the following table:

Table 4

| Shaped piece according to Example | Time elapsed before 100% of the animals were lying on their backs (hours) |
|---|---|
| 6 | 2 |
| 6a | 5 |

It will be appreciated that the instant specification and examples are set forth by way of illustration and not limitation, and that various modifications and changes may be made without departing from the spirit and scope of the present invention.

What is claimed is:

1. An insecticidal preparation having a depot gas action and comprising an insecticidally effective amount of dimethyl-2,2-dichlorovinyl thiophosphate in admixture with an unsaturated polyester copolymer resin as carrier, the resin being a condensation product of maleic anhydride, phthalic anhydride, propanediol, dipropylene glycol and styrene, whereby the preparation exhibits extended insecticidal activity.

2. A preparation according to claim 1, further including at least one auxiliary or filler selected from the group consisting of plasticizers, stabilizers, vaporization promoters, vaporization inhibitors, glass fibers, textile fibers, pigments, dyestuffs, scents and quartz.

3. A preparation according to claim 1 contained in a casing which adjustably provides for full or reduced release of the gassing agent.

4. A method of excluding insects from a predetermined area which comprises placing in such area an insecticidal preparation according to claim 1.

5. A method according to claim 4, in which the insects are flies.

* * * * *